(12) United States Patent
Hata et al.

(10) Patent No.: US 8,496,573 B2
(45) Date of Patent: Jul. 30, 2013

(54) STEERABLE CAPSULE APPARATUS AND METHOD

(75) Inventors: Nobuhiko Hata, Waban, MA (US); Peter Jakab, Brookline, MA (US); Gabor Kosa, Pregassona (CH); Ferenc Jolesz, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 322 days.

(21) Appl. No.: 12/600,163

(22) PCT Filed: May 16, 2008

(86) PCT No.: PCT/US2008/063972
§ 371 (c)(1),
(2), (4) Date: Aug. 9, 2010

(87) PCT Pub. No.: WO2008/144559
PCT Pub. Date: Nov. 27, 2008

(65) Prior Publication Data
US 2010/0298635 A1    Nov. 25, 2010

Related U.S. Application Data

(60) Provisional application No. 60/938,909, filed on May 18, 2007.

(51) Int. Cl.
*A61B 1/05* (2006.01)
*A61B 5/05* (2006.01)
*A61B 1/00* (2006.01)

(52) U.S. Cl.
USPC .......................................................... 600/101

(58) Field of Classification Search
USPC ........................................................... 600/101
See application file for complete search history.

(56) References Cited

U.S. PATENT DOCUMENTS

| 7,697,970 B2* | 4/2010 | Uchiyama et al. ............ 600/407 |
| 2006/0063974 A1* | 3/2006 | Uchiyama et al. ............ 600/114 |
| 2006/0169293 A1* | 8/2006 | Yokoi et al. ................... 128/899 |
| 2009/0264702 A1* | 10/2009 | Yoshizawa ..................... 600/117 |
| 2009/0275801 A1* | 11/2009 | Sakai ............................. 600/117 |

FOREIGN PATENT DOCUMENTS

| EP | 1591057 A1 | 11/2005 |
| EP | 1618830 A1 | 1/2006 |

(Continued)

OTHER PUBLICATIONS

Chris H. Wiggins and Raymond E. Goldstein, Flexive and Propulsive Dynamics of Elastica at Low Reynolds Number, The American Physical Society vol. 80, No. 17, 1998.*

(Continued)

*Primary Examiner* — Clayton E LaBalle
*Assistant Examiner* — Kevin Butler
(74) *Attorney, Agent, or Firm* — Fitch, Even, Tabin & Flannery

(57) ABSTRACT

A capsule includes a main body with at least one tail connected to the main body. At least two coils are disposed on each tail such that the coils are responsive to a magnetic field interacting with the coils such that a force is exerted on the tail. The capsule is controlled through application of a varying magnetic field with a constant current in the coils and/or by providing varying a current in the coils that interact with a constant magnetic field. The capsule can be disposed in a cavity, and the magnetic field can be provided from outside the cavity to affect movement of the capsule. An MRI device can be configured to control and image the capsule.

25 Claims, 3 Drawing Sheets

FOREIGN PATENT DOCUMENTS

| | | | |
|---|---|---|---|
| JP | 2001-179700 | * | 7/2001 |
| JP | EP1591057 | * | 5/2003 |
| KR | 20040110566 | * | 12/2004 |
| KR | 20060013519 A | | 2/2006 |
| WO | 2004066830 A1 | | 8/2004 |
| WO | WO2011058505 | * | 5/2011 |

OTHER PUBLICATIONS

Seiichi Sudo, Micro Swimming Robots Based on Small Aquatic Creatures, Akita Perfectural University, Japan, Mar. 1, 2010.*

Sowjanyastanns, Swimming Robots in Medicine, http://www.pharmainfo.net/sowjanyastanns/swimmings-robots-medicine, Sat, May 1, 2010—16:14.*

Jonathan Strickland, How Nanorobots Will Work, howstuffworks.com; http://electronics.howstuffworks.com/nanorobot.htm, Jan. 9, 2011.*

Gabor Kosa et al., Flagellar Swimming for Medical Micro Robots: Theory, Experiments and Application, Proceedings of the 2nd Biennial IEEE International Conference on Biomedical Robitics and Biomechatronics, Oct. 19-22, 2008.*

Michael W. Wybenga, Design of a Propulsion System for Swimming Under Low Reynolds Flow Conditions, Thesis presented to University of Waterloo, Ontario, Canada, 2007.*

Abott et al. How Should Microrobots Swim?, The International Journal of Robotics Research, vol. 00, No. 00, Jul. 31, 2009.*

Nelson et al, Microrobots for Minimally Invasive Mediciine, The Annual Review of Biomedical Engineering, http://bioeng.annualreviews.org, 2010.*

Guo et al, Development and Experiments of a Bio-inspired Underwater Microrobot with 8 Legs, Harbin Engineering University, Osaka Japan 2010.*

Temel, Magnetically Actuated Micro Swimming of Bio-inspired Robots in Mini Channels, Mechatronics Program, Sabanci University, Istanbul, Turkey Apr. 2011.*

International Search Report for PCT/US2008/063972, Nov. 10, 2008.

Jung Jae Hun et al.; English Language Abstract for 20040110566KR; Dec. 31, 2004.

ASTM (2000). "Standard Test Method for Evaluation of MR Image Artifacts from Passive Implants," A. International, ASTM Committee F04.15 on Material Test Methods. ASTM F2119-01.

Colgate, J. E., K. M. Lynch (2004). "Mechanics and control of swimming: A review." IEEE Journal of Oceanic Engineering 29(3): 660-673.

Dimaio, S. P., D. F. Kacher, et al. (2006). "Needle artifact localization in 3T MR images." Stud Health Technol Inform 119: 120-5.

Dimaio, S. P., S. Pieper, et al. (2006). "Robot-assisted needle placement in open-MRI: system architecture, integration and validation." Stud Health Technol Inform 119: 126-31.

Fukuda, T. (1994). "Mechanism and Swimming Experiment of Micro Mobile Robot in Water," Proc. of IEEE Intl Workshop on Micro Electro Mechanical Systems (MEMS '94): 273-278.

Gandhi, O. P., X. B. Chen (1999). "Specific absorption rates and induced current densities for an anatomy-based model of the human for exposure to time-varying magnetic fields of MRI." Magn Reson Med 41(4): 816-23.

Guo, S., Y. Hasegawa, et al. (2001). "Fish-like underwater microrobot with multi DOF" International Symposium on Micromechatronics and Human Science.

Guo, S. X., T. Fukuda, et al. (2003). "A new type of fish-like underwater microrobot." IEEE-Asme Transactions on Mechatronics 8(1): 136-141.

Hata, N., Dohi, T., et al. (1997). "Development of a frameless and armless stereotactic neuronavigation system with ultrasonographic registration." Neurosurgery 41(3): 608-13; discussion 613-4.

Hata, N., Jinzaki, M., et al. (2001). "MR imaging-guided prostate biopsy with surgical navigation software: Device validation and feasibility." Radiology 220(1): 263-268.

Hata, N., Nabavi, A., et al. (1999). "A volumetric optical flow method for measurement of brain deformation from intraoperative magnetic resonance images." Medical Image Computing and Computer-Assisted Intervention, Miccai '99, Proceedings. 1679: 928-935.

Hata, N., A. Nabavi, et al. (2000). "Three-dimensional optical flow method for measurement of volumetric brain deformation from intraoperative MR images." J Comput Assist Tomogr 24(4): 531-8.

Hirose, M., A. Bharatha, et al. (2001). "Quantitative MRI assessment of prostate gland deformation before and during MRI-guided brachytherapy." Radiology 221: 224-224.

Honda, T., K. I. Arai, et al. (1996). "Micro swimming mechanisms propelled by external magnetic fields." IEEE Transactions on Magnetics 32(5): 5085-5087.

Sendoh, M., K. Ishiyama, et al. (2003). "Fabrication of magnetic actuator for use in a capsule endoscope." IEEE Transactions on Magnetics 39(5): 3232-3234.

Sudo, S., R. Orikasa, et al. (2004). "Locomotive characteristics of swimming mechanism propelled by alternating magnetic field." International Journal of Applied Electromagnetics and Mechanics 19(1-4): 263-267.

K. B. Yesin, P., Exner, K. Vollmers, B. J. Nelson, "Design and Control of In-Vivo Magnetic Microrobots", Proc. 8th International Conference on Medical Image Computing and Computer Assisted Intervention (MICCAI), Palm Springs, USA, Oct. 2005.

G. Kosa, M. Shoham, M. Zaaroor, "Propulsion of a Swimming Micro Medical Robot," IEEE Conference on Robotics and Automation (ICRA '05), pp. 1339-1343, Apr. 2005.

G. Kosa, M. Shoham, M. Zaaroor, "Analysis of a Swimming Micro Medical Robot", IEEE/RAS-EMBS International Conference on Biomedical Robotics and Biomechatronics (BioRob 2006), pp. 131-135, Feb. 2006.

G. Kosa, M. Shoham, M. Zaaroor., "Propulsion Method for Swimming Micro Robots", IEEE Transaction on Robotics, vol. 23, No. 1, Feb. 2007.

Iddan, G., Meron, G., Glukhovsky, A., Swain, P., "Wireless capsule endoscopy." Nature 405, (2000) 417.

Ell C., Reinke, S., May, A., Helou, L., Henrich, R., Mayer, G., "The first prospective controlled trial comparing wireless capsule endoscopy with push enteroscopy in chronic gastrointestinal bleeding." Endoscopy 34, (2002) 685-689.

Stefanini, C., Menciassi, A. Dario, P., "Modeling and experiments on a legged microrobot locomoting in a tubular, compliant and slippery environment," International Journal of Robotics Research 25(5-6), (2006) 551-560.

Gorini S., Quirini M., Menciassi A., Pemorio, G., Stefanini, C, and Dario P., "A Novel SMA Based Actuator for a Legged Endoscopic Capsule," Proceeding of IEEE/RAS—EMBS International Conference on Biomedical Robotics and Biomechatronics, (2006).

Taylor, G., "The action of waving cylindrical tails in propelling microscopic organisms," Proceedings of the Royal Society A, (1952) 225-239.

Kosa, G., Shoham, M., Zaaroor M., "Propulsion Method for Swimming Microrobots," IEEE Transactions on Robotics, 23(1), (2007) 137-150.

* cited by examiner

STEERABLE CAPSULE APPARATUS AND METHOD

RELATED APPLICATION(S)

This application claims the benefit of U.S. Provisional application No. 60/938,909, filed May 18, 2007, which is incorporated by reference in its entirety herein.

TECHNICAL FIELD

This invention relates generally to capsules or pills for use in a body for medical purposes and more specifically to steerable such capsules or pills.

BACKGROUND

Various methods of direct exploration of body cavities are known for medical diagnosis and treatment. One example is the capsule endoscope, which has been used in the diagnosis of small intestine bleeding and detection of Crohn's Disease, Celiac disease, and other malabsorption disorders, as well as benign and malignant tumors of the small intestine. The capsule endoscope includes essentially a camera in a pill form that the subject swallows. As the capsule passes through the digestive tract of the subject, the camera captures many pictures of the tract. After the capsule passes out of the subject, the pictures are retrieved and analyzed. The capsule endoscope can reach areas of the small intestine that a conventional endoscope cannot.

Although capsule endoscopy is an improved technique for detecting sources of small bowel bleeding, it does not achieve 100% detection. The capsule is purely diagnostic and cannot be used to take biopsies, apply therapy, or mark abnormalities for surgery. Moreover, the capsule cannot be controlled once it has been ingested, so that its progress cannot be slowed to better visualize a suspicious abnormality.

Swimming capsules are an advanced version of capsule (also called a swimming micro-robot) that can be actively positioned by propulsion. One such device included piezoelectric actuators based on ionic conducting polymer film. A later similar device included a symmetrical structure with four fins that allowed the micro-robot to turn as well as swim. Changing the frequency of one of the two piezoelectric actuators enabled turning.

Another known approach includes a micro-robot powered by a static magnetic field. The swimming mechanism in this approach included a helix tail in an alternating magnet field generated by a physically rotating permanent magnet. The micro-robot was made of a spiral copper wire and a SmCo permanent magnet attached to its tip. By applying an external alternating magnetic field, magnetic torque can be created at the tip of the spiral copper wire. Alternatively, an electrically generated magnetic field could be used.

Yet another known approach includes using a magnetic actuator composed of a magnet and spiral structure that can be moved wirelessly by applying an external magnetic field. The magnetic actuator in this approach was composed of a capsule dummy, a permanent magnet inside the capsule, and a spiral structure. The actuator was rotated and propelled wirelessly by applying an external rotational magnetic field. The capsule, however, can only move forwards or backwards in the gastro-intestinal ("GI") tract and depends on the assumption that the capsule always has contact with the GI tract. Thus, three-dimensional position and orientation control of the capsule is not possible, prohibiting the range of its application in GI tract.

Another disadvantage to previous approaches is that the location of the previous swimming micro-robots could not be determined during examination. Magnetic resonance imaging ("MRI"), a minimally invasive yet comprehensive imaging technology, may provide this capability; however, the above approaches used ferro-magnetic materials such as a permanent magnet in the capsule and rotating local magnetic fields to generate propulsion. Such propulsive mechanisms cannot be combined with MRI due to the interaction of the ferro-magnetic material with an MRI's magnetic field. It is also difficult to place an additional set of magnetic field generators inside an MRI device and also virtually any other medical imaging device.

BRIEF DESCRIPTION OF THE DRAWINGS

The above needs are at least partially met through provision of the steerable capsule apparatus and method described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION OF THE PREFERRED EMBODIMENT(S)

Generally speaking, pursuant to these various embodiments, a capsule generally includes a main body with at least one tail connected to the main body. The main body may include any of several elements useful in various medical applications. The tail(s) may extend from the main body or be positions near and/or along the main body. At least two coils are disposed on each tail such that the coils are responsive to a magnetic field interacting with the coils such that a force is exerted on the tail. Typically, each coil includes a number of turns and a surface area such that each coil has a resonant frequency. The capsule may be controlled through application of a magnetic field. The capsule can be disposed in a cavity, and the magnetic field can be provided from outside the cavity to affect movement of the capsule.

So configured, the capsule can be steered through a body cavity that can be simultaneously imaged by, for example, an MRI device because the capsule does not require ferro-magnetic elements to be incorporated within its body. Advantageously, the capsule can be controlled though the use of magnetic field generators inherently available in a typical MRI device. Accordingly, the capsule can be imaged at the same time as the cavity, and an image of the cavity can be marked with the capsule location. In this manner, areas of interest may be marked for follow up treatment or investigation. Similarly, the capsule can be directed to an area of interest discovered during an imaging session for more direct investigation or immediate treatment.

Figure 1:
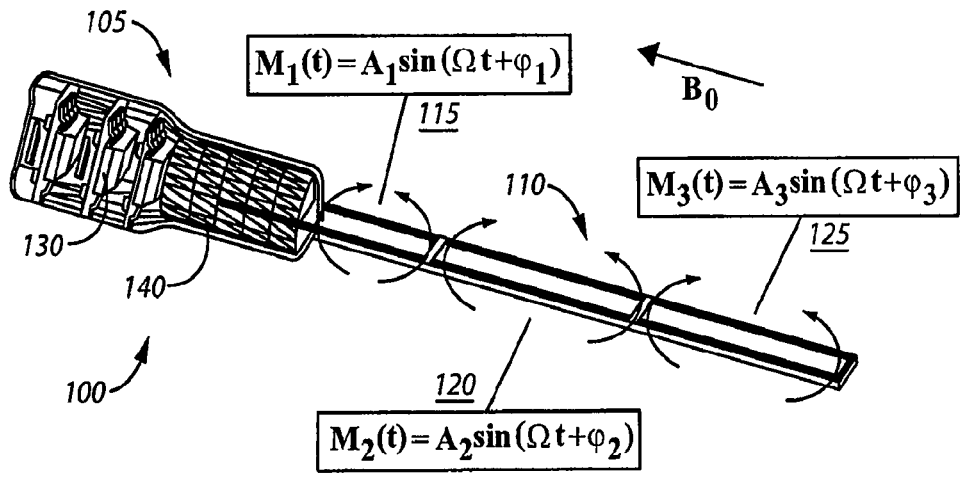
FIG. 1 comprises a perspective view of an example one tail capsule as configured in accordance with various embodiments of the invention.

These and other benefits may become clearer upon making a thorough review and study of the following detailed description. Referring now to the drawings, and in particular to FIG. 1, an illustrative steerable capsule 100 apparatus for maneuvering within a small space includes a main body 105 with at least one tail 110 connected to the main body 105 such that the at least one tail 110 extends distally from the main body 105. At least two coils 115, 120, and 125 are disposed on each tail 110 such that the coils 115, 120, and 125 are responsive to a magnetic field interacting with the coils. The interactions with the magnetic field result in a force exerted on the tail(s) 110.

A control circuit, also referred to as a driving circuit 130, communicates with the coils 115, 120, and 125 to provide a current to the coils to affect interaction with the magnetic field and to control the forces exerted on the tail(s) 110. The driving circuit 130 can comprise a fixed-purpose hard-wired platform or can comprise a partially or wholly programmable platform to perform the controlling and driving methods described herein. All of these architectural options are well known and understood in the art and require no further description here. A power source 140, such as a battery, may be included in the capsule 100, or the capsule 100 may be powered through currents generated in the coils 115, 120, 125 by externally applied magnetic fields. The control or driving circuitry 130 or separate circuitry can be configured by one skilled in the art to control the collection and provision of such power in the capsule 100.

Motion is generated for the capsule 100 by placing a conductive element, here the coils 115, 120, and 125, carrying electric current into a static magnetic field $B_0$, as may be applied, for example, by an MRI device. The interaction between the current carrying element and the magnetic field creates a force on the current carrying element. By alternating the direction of the current in the coils 115, 120, and 125 or by varying a magnetic field applied to the coils 115, 120, and 125, a back and forth type of force and motion may be created. The Lorentz Force Law, having the equation $F=q(E+v\times B)$, describes the force F, exerted on the charged particles moving in the coils 115, 120, and 125 in the presence of electric and magnetic fields.

Figure 2:
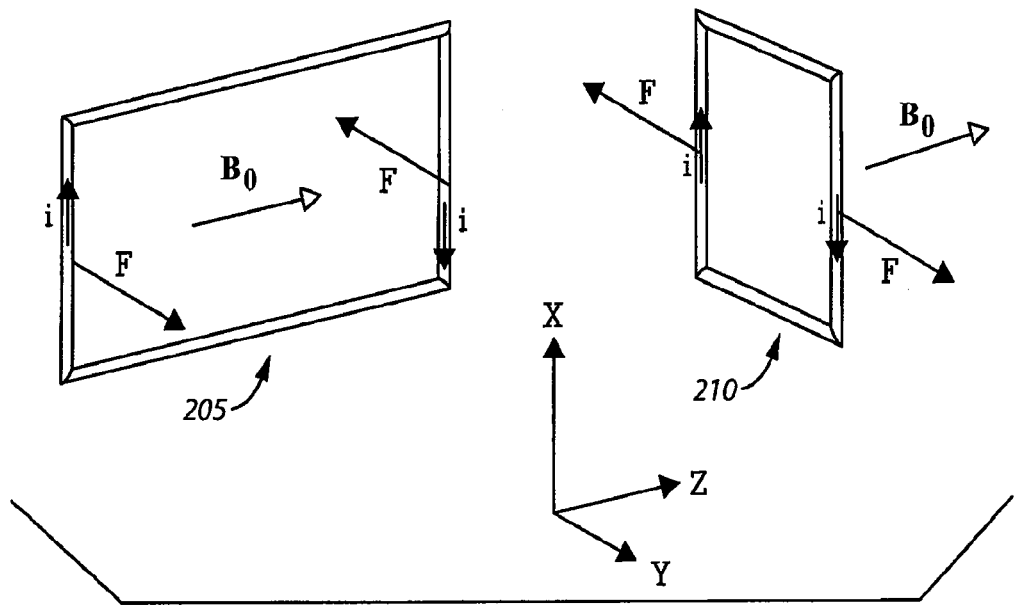
FIG. 2 comprises a perspective views of two example coils with an indication of the current and forces for the coils as configured in accordance with various embodiments of the invention.

For this force equation, q is the charge of the particle, v is the speed of the particle, E is the electric field intensity felt by the particle, and B ($B=\mu_0 H$) is the magnetic field intensity felt by the particle. Because the current created by the charged particles needs to form a closed loop to flow, the force F acts along the current path of the conductive wire loop forming the coils 115, 120, and 125. Diagrams of similar coils 205 and 210 with indications of the forces F, charge i flowing through the coils 205 and 210, and applied magnetic field $B_0$ are illustrated in FIG. 2. In these coils, a magnetic field is created when the charge or current i flows circularly through the coils. The magnetic field created by the current flow experiences a force tending to align with the external magnetic field $B_0$. Accordingly, the coil 205 that is in line with the magnetic field $B_0$ experiences a force F tending to rotate the coil 205 such that it ends up perpendicular to the magnetic field $B_0$, as shown in coil 210. The forces F experienced by the coil 210 cancel each other such that the coil 210 remains substantially perpendicular to the applied magnetic field $B_0$.

With reference to FIG. 1, such forces can be used in one approach to controlling movement of the capsule 100 in a fluid or small space environment. A current is provided to the coils 115, 120, 125 disposed on the tail(s) 110 coupled to a main body 105 of the capsule 100. The current is controlled so as to control interaction between the coils 115, 120, 125 and a magnetic field applied to the coils 115, 120, 125. The current can be varied to affect varying forces on the coils 115, 120, 125 to affect bending of each tail 100 having coils 115, 120, 125 receiving the current. By another approach, a substantially constant current is provided to the coils 115, 120, 125 to affect interaction between coils 115, 120, 125 receiving the current and the magnetic field applied to the coils 115, 120, 125. For example, the capsule 100 may be rotated without lateral movement by applying a constant current to the coils 115, 120, and 125 and wherein the applied magnetic field is a constant magnetic field that aligns the capsule 100 with respect to the constant magnetic field. The constant current in combination with the applied magnetic field $B_0$ creates a torque on the coils 115, 120, and 125 as described above with reference to FIG. 2, thereby turning the entire capsule 100 in such a way that the axis (normal) of the coils tends to be aligned with the direction of the static magnetic field $B_0$.

To generate a propulsive force, at least two coils 115, 120, and 125 are placed on an elongated tail 110, and the capsule 100 having the tail 110 is surrounded with fluid. Each of the coils 115, 120, and 125 is driven by a current with each coil's current having a particular sinusoidal waveform crafted for propulsive force. The current with a sinusoidal waveform can be created by the control or driving circuitry 130 in the capsule 100 or by the coils' interaction with external varying magnetic fields applied to the capsule 100 by external devices, such as an MRI machine or other magnetic field generator(s). The waveform amplitude and the phase may be different for each coil 115, 120, and 125, while the frequencies for the coils 115, 120, and 125 may have the same value. The interaction between the static magnetic field $B_0$ applied from outside the capsule 100 and the current flowing in the coils 115, 120, and 125 creates a time and location dependent bending along the tail 110. The phases and amplitudes of the waveforms are optimized to create a traveling wave in the tail 110. This traveling wave exerts a propulsive force on the fluid surrounding the tail 110 and creates linear forward motion for the capsule 100. This propulsion method is able to move a payload in the direction of the static magnetic field of the MRI, which is difficult to achieve with different propulsion methods.

A capsule 100 with a single tail 110 as shown in FIG. 1 is able to move in one direction. To maneuver in a two-dimensional plane, two tails are necessary, and to move in a three-dimensional space at least three tails are needed as shown for example in FIG. 3. Each tail in these embodiments provides substantially forward propulsion; therefore, by driving all three tails 310, 320, and 330 with the same signal, the capsule 340 will advance in the Z direction. Applying different amplitude signals for each tail 310, 320, and 330 enables advancing and turning into any direction.

By one approach to controlling the propulsion, with reference again to FIG. 1, an MRI machine may apply the external magnetic fields. During the operation of an MRI, two kinds of magnetic fields are introduced into the region in addition to the static magnetic field across the region. One of the fields is a gradient magnetic field; the other is a radio frequency ("RF") magnetic field. Because these magnetic fields are changing in time, they induce a current in the coils 115, 120, and 125. Faraday's Induction Law describes the relationship between the electric field E driving the current in the coils and the magnetic field B:

$$\oint_L E dl = \frac{\partial}{\partial t} \int_A B \, dA$$

The line L encloses the surface area A of each coil 115, 120, and 125. This equation shows that the varying magnetic fields applied to the capsule 100 will induce varying currents in the coil 115, 120, and 125. Accordingly, a varying magnetic field can induces a varying current in the at least two coils, and at least one of the coils can be connected to the main body 105 such that the current provides power to at least a portion of the main body 105. For example, the driving circuitry 130 can be powered by the current such that the driving circuitry 130 controls the tail 110. In one approach, the sinusoidal time varying nature of the RF magnetic field can be a power source for the capsule 100 because the RF signal can induce a varying electric current in the coils 115, 120, and 125 that can power the capsule 100 using circuitry known to those skilled in the art connected to the coils 115, 120, and 125 to rectify the induced current and redistribute that energy in the capsule 100. Additional coils may be provided perpendicular to the coils 115, 120, 125 such that power is still provided by the external magnetic field when the field is in the same plane as the coils 115, 120, 125. When it is not practical to utilize an MRI sourced RF magnetic field as a power source, a similar external varying magnetic field may be substituted. By another approach to powering the capsule 100, batteries 140 may be included in the capsule 100. For example, standard hearing aid batteries can be incorporated into the capsule 100.

The induced electromotive force EMF on a coil having a surface area A and number of turns N from a magnetic field B having a frequency $\omega$ can be described with the following equation:

$$EMF = -NAB \frac{\partial}{\partial t} \sin(\omega t).$$

When the coil has an electric load forming a closed electric circuit of total electrical resistance R, an electric current i will flow in the coil in reaction to the applied magnetic field according to the following equation:

$$Ri = EMF = -NAB \frac{\partial}{\partial t} \sin(\omega t).$$

The current created in the coil may then be utilized for propulsive purpose. In this approach, the externally applied magnetic field comprises a sinusoidal-varying magnetic field that induces a variable current in the at least two coils that induces varying deformation substantially in accordance with a sinusoidal waveform in the at least one tail. In this approach, the current in the coils can remain constant where the varying current is applied by the external magnetic field. In a variation on this approach, the driving circuitry can vary the resistive load on the coil to create the right amount of current flow in reaction to the applied field.

By another approach, the applied magnetic field may be static, and the driving circuitry is configured to provide a varying current to the at least two coils such that the interaction with the magnetic field affects varying forces on the at least one tail and varying deformation in the at least one tail. Here, the sinusoidal variation can be controlled and applied by the driving circuitry instead of by the controls of the externally applied magnetic field, such as from an MRI device. By any of these approaches, the forces applied to the coils 115, 120, and 125 can move or flex the tail 110 portions in a wave-like manner to promote movement of the capsule 100.

One approach to calculating the frequency and current ranges for the coils 115, 120, and 125 and the applied magnetic fields to affect propulsion will now be described. Due to scaling effects in the hydrodynamic equations that describe how the capsule 100 travels in a fluid, the swimming action in the micro world is different from macro size swimmers. In fluid mechanics and aerodynamics, the Reynolds number is a measure of the ratio of inertial forces to viscous forces, and consequently, it quantifies the relative importance of these two types of forces for given flow conditions. In micro flows that form the typical environment for the capsule 100, the Reynolds numbers are low (Re<1) thereby enabling the omission of the inertial terms from the Navier-Stokes equations and confining the equations to the viscous flow environment. In addition, the linearity of the Stokes equations in the viscous flow environment generally prohibits the use of repeated motion such as that of the fish tail in the micro-mechanism to generate propulsion force. Swimming in the viscous flow is achievable instead through undulatory action. Following a known theoretical model and inspired by the flagellar movement of microorganisms, the oscillating beam of the tail 110 can create an approximated sinusoidal traveling wave in viscous flow and produces propulsion force effectively. The sinusoidal wave from the tail 110 can be described with the following equation:

$$w^{(d)}(x, t) = w \sin\kappa(x - Ut)$$
$$= w(\sin\kappa x \cos\kappa Ut - \cos\kappa x \sin\kappa Ut) =$$
$$= \sum_{k=1}^{\infty} (Cs_k \cos\kappa Ut - Cc_k \sin\kappa Ut)\phi_k(x)$$
$$= \sum_{k=1}^{\infty} g_k^{(d)}(t)\phi_k(x) \approx \sum_{k=1}^{3} G_k \sin(\Omega t - \Phi_k)\phi_k(x)$$

where w, $\kappa$, and U are respectively the amplitude, wave number, and wave velocity of the desired advancing wave in the tail 110. $Cs_k$ and $Cc_k$ are the decomposition of sin kx and cos kx into the modal functions, $\phi_k(x)$, of the k-th mode of the tail. The function $g_k^{(d)}(t)$ is the desired time function of the k-th mode to be achieved in the tail 110 to affect the desired traveling wave $w^{(d)}(x,t)$.

These equations may be extended to an elongated tail 110 with multiple coils 115, 120, and 125 attached in a row. The number of coils 115, 120, and 125 in a tail 110 is equal to the number of controllable time functions $g_k^{(d)}(t)$. At least two coils 115, 120, and 125 are needed to create undulatory motion in the tail 110. Using a large number of coils 115, 120, and 125 increases the driving frequency but can add additional technological difficulties. One approach illustrated in FIG. 1 includes using three coils 115, 120, and 125 in a row for the swimming tail 110. To create the phases $\Phi_k$ and amplitudes $G_k$, one has to take into consideration the tail's dynamical response. Accordingly, the above equation can be solved to determine the input currents that can create the amplitudes $\{G_1, G_2, G_3\}$ and phases $\{\Phi_1 \Phi_2 \Phi_3\}$ for the above equation that will cause the tail 110 to vibrate in a sinusoidal traveling wave.

The tail's vibration can be divided into three segments corresponding to the coils 115, 120, and 125 on the tail 110: $w_1(x,t)$ is the lateral motion of the tail 110 in the area bounded by the coil 115 closest to the main body 105 defined by $x=[0,\alpha_1 L]$; $w_2(x,t)$ is the lateral motion at the middle coil 120 where $x=[\alpha_1 L, \alpha_2 L]$; and $w_3(x,t)$ is the lateral motion at the coil 125 therein the end of the tail 110 where $x=[\alpha_2 L, L]$. The motion of the tail 110 is governed by the Euler-Bernoulli beam equations:

$$m_1 \frac{\partial^2 w_1(x,t)}{\partial t^2} + c \frac{\partial w_1(x,t)}{\partial t} + \hat{K}_1 \frac{\partial^4 w_1(x,t)}{\partial x^4} = 0 \forall x = [0, \alpha_1 L]$$

$$m_2 \frac{\partial^2 w_2(x,t)}{\partial t^2} + c \frac{\partial w_1(x,t)}{\partial t} + \hat{K}_2 \frac{\partial^4 w_2(x,t)}{\partial x^4} = 0 \forall x = [\alpha_1 L, \alpha_2 L]$$

$$m_3 \frac{\partial^2 w_3(x,t)}{\partial t^2} + c \frac{\partial w_1(x,t)}{\partial t} + \hat{K}_3 \frac{\partial^4 w_3(x,t)}{\partial x^4} = 0 \forall x = [\alpha_2 L, L]$$

where $m_i$ is the distributed mass of each tail 110 segment, c is the damping coefficient and $\hat{K}_1$ is the elastic stiffness of each segment. The definition for each of these elements is known.

The boundary conditions of the tail 110 then can be described with the following equations:

$$\text{at } x = 0: \hat{K}_1 \frac{\partial^2 w_1(0,t)}{\partial x^2} = -K_\theta \frac{\partial w_1(0,t)}{\partial x} \text{ and}$$

$$\hat{K}_1 \frac{\partial^3 w_1(0,t)}{\partial x^3} = -K w_1(0,t) + F_{L1}(t); \text{ and}$$

$$\text{at } x = L: \frac{\partial^2 w_3(0,t)}{\partial x^2} = 0 \text{ and}$$

$$\hat{K}_3 \frac{\partial^3 w_3(0,t)}{\partial x^3} = -F_{L3}$$

where $K_\theta$ is the spring coefficient of an angular spring located at the base of the tail 110 and K is the coefficient of a linear spring located at the base of the tail 110. $K_\theta$ and K were added to the theoretical formulation to overcome the uncertainty of the tail clamping for the capsula 100, and they are calibrated empirically. The Lorenz force created by the magnetic field is described by the equation $F_{Li}(t) = N_i b_i I_i(t) B_0$ where $B_0$ is the magnetic field, $N_i$ is the number of turns in the i-th coil, $B_i$ is the width of the coil, and $I_i(t)$ is the current in the coil.

The continuity conditions at the boundaries between two coils are then described by the following:
at $x=\alpha_1 L$ between coil 115 and coil 120:

$$w_1(\alpha_1 L, t) = w_2(\alpha_1 L, t)$$

$$\hat{K}_1 \frac{\partial^2 w_1(\alpha_1 L, t)}{\partial x^2} = \hat{K}_2 \frac{\partial^2 w_2(\alpha_1 L, t)}{\partial x^2}$$

$$\hat{K}_1 \frac{\partial^3 w_1(\alpha_1 L, t)}{\partial x^3} + F_{L1}(t) = \hat{K}_2 \frac{\partial^3 w_2(\alpha_1 L, t)}{\partial x^3} + F_{L2}(t)$$

and at $x=\alpha_2 L$ between coil 120 and coil 125:

$$w_2(\alpha_1 L, t) = w_3(\alpha_1 L, t)$$

$$\frac{\partial w_2(\alpha_2 L, t)}{\partial x} = \frac{\partial w_3(\alpha_2 L, t)}{\partial x}$$

$$\hat{K}_2 \frac{\partial^2 w_2(\alpha_2 L, t)}{\partial x^2} = \hat{K}_3 \frac{\partial^2 w_3(\alpha_2 L, t)}{\partial x^2}$$

$$\hat{K}_2 \frac{\partial^3 w_2(\alpha_2 L, t)}{\partial x^3} + F_{L2}(t) = \hat{K}_3 \frac{\partial^3 w_3(\alpha_2 L, t)}{\partial x^3} + F_{L3}(t)$$

To solve the above equations by a separation of variables method, one has to convert the boundary conditions. The conversion will result in a set of polynomials in the field equation and homogeneous boundary and continuity conditions. The solution of the problem has the following form:

$$w_i(x,t) = \sum_{k=1}^{\infty} \phi_k^{(i)}(x) g_k(t) \forall i = 1, 2, 3$$

In this solution, $\phi_k^{(i)}(x)$ is the shape of the k-th modal function in the tail segment i, and $g_k(t)$ is the time function of the k-th mode of the tail 110. In the converted problem, the modes and the natural frequencies are found, and the partial differential equations for the boundary conditions are converted to an infinite set of ordinary differential equations with one differential equation for each mode. The ordinary differential equations are already presented in the Laplace s-domain because the steady state solution of problem provides the information needed for operating the tail 110. The general form of the time function is:

$$g_k(s) = -\left( 1 + \frac{s(s + 2\xi_k^{(1)} \omega_k)}{s^2 + 2\xi_k^{(1)} \omega_k s + \omega_k^2} + \frac{s(s + 2\xi_k^{(2)} \omega_k)}{s^2 + 2\xi_k^{(2)} \omega_k s + \omega_k^2} + \frac{s(s + 2\xi_k^{(3)} \omega_k)}{s^2 + 2\xi_k^{(3)} \omega_k s + \omega_k^2} \right) \sum_{i=1}^{3} Cp_k^{(i)} F_{Li}(s) \forall k = 1, 2, \ldots, \infty$$

The function $\xi_k^{(i)} \forall k=1, 2, \ldots, \infty$ is the damping ratio in the i-th segment of the k-th mode, $\omega_k$ is the natural frequency of the k-th mode, and $Cp_k^{(i)}$ is the decomposition of the polynomial that was used to convert the problem in the earlier steps of the solution.

Figure 4:
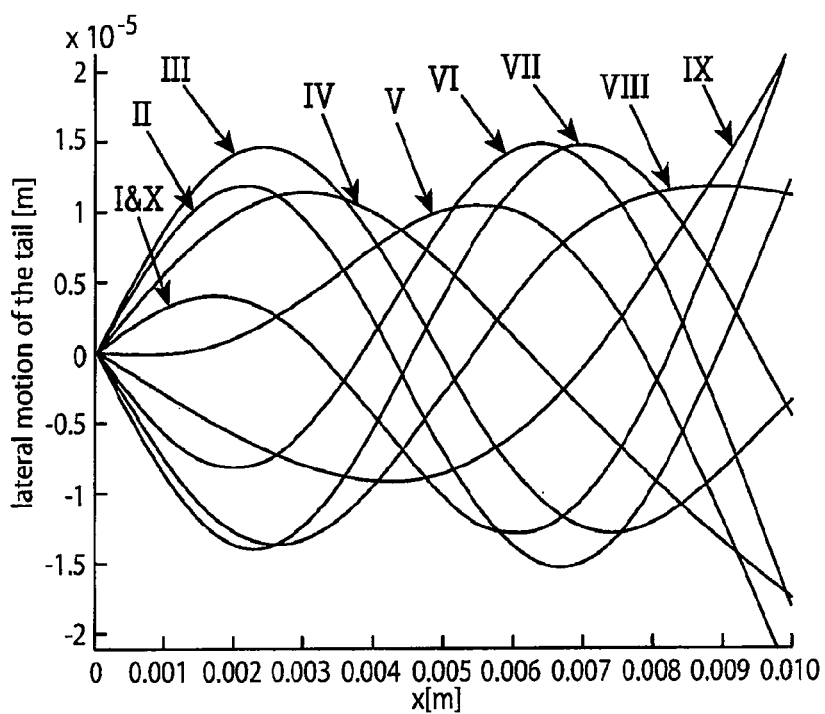
FIG. 4 comprises a graphic illustration of the motion of an example capsule tail by sequel snapshots of a tail simulation at ten different time points I through X.

Because there are three inputs to the system $u=[Fu(s), Fu(s), F_{L1}(s)]^T$, a three-time function can be controlled $y=[g_1(s), g_2(s), g_3(s)]^T$. The above time function is truncated at the third mode for a three coil system to create a three by three square multiple input-multiple output system, $y=P(s)u$. From the transfer matrix, P(s), an input u can be found that gives the desired output, $y=[g_1^{(d)}(s), g_2^{(d)}(s), g_3^{(d)}(s)]^T$ and activates the tail 110 by open loop control. Further details on the calculation of the amplitudes $\{G_1, G_2, G_3\}$ and phases $\{\Phi_1 \Phi_2, \Phi_3\}$ are known and available in the article Kósa, G., Shoham, M. and Zaaroor M., Propulsion of a Swimming Mirco Medical Robot, IEEE Conference on Robotics and Automation (ICRA05), (2005) 1339-1343, which is incorporated in its entirety herein. The above equations can be readily implemented in software or firmware in the capsule circuitry and/or in the external magnetic field generators to control the application of magnetic fields and/or current to the coils 115, 120, and 125 to control the movement of the tail 110. FIG. 4 illustrates a simulation of the motion created in the tail 110 by the input forces calculated from the above multiple input-multiple output system based on the equation for $g_k(s)$ above.

More specifically, in one approach, the patient or subject swallows the capsule, and a gastroenterologist maneuvers it using magnetic fields generated by an MRI device in combination with MRI imaging guidance, monitoring, and/or mapping. The capsule can be extremely small and have no attached tethering. For example, a capsule built according to these teachings can range in size between about 3 and about 30 millimeters in length and between about 3 and about 15 millimeters in diameter, depending on the payload or tools carried in the capsule. Example tools that may be carried in the capsule include a small camera, a biopsy tool, a small container in combination with a micro pump and a micro valve, a communication device, an electrode, and at least one operating tool. Such micro-sized cameras and communication devices are known and available commercially. In one example combination, a camera, communication device, and power source can be disposed in a main body of the capsule with a size of about 11 millimeters in diameter and 27 millimeters in length. In another example, a camera having a size of 3.5 millimeters in diameter and 12 millimeters in length can be disposed in the main body of the capsule.

Figure 3:
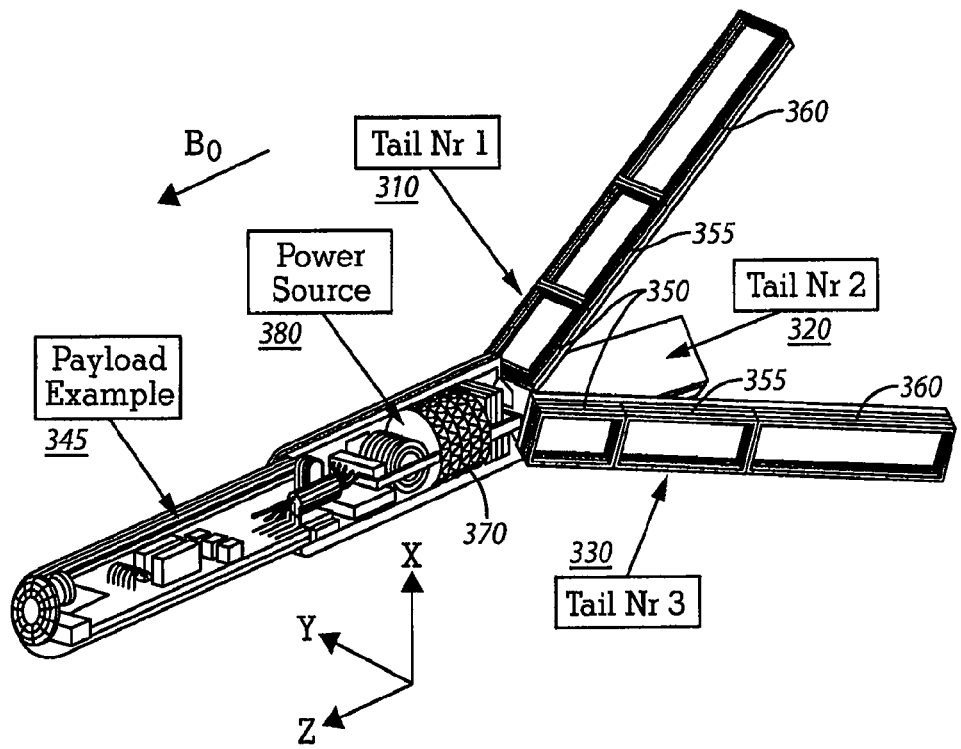
FIG. 3 comprises a perspective view of an example three-tail capsule as configured in accordance with various embodiments of the invention.

With reference to FIG. 3, in another example, a capsule 340 includes a camera 345 and three tails 310, 320, and 330 connected to the main body 305, each tail having a 10 millimeter length, 1.5 millimeter width, and 0.15 millimeter thickness (about 0.2 millimeter including the coils). In this example, each tail 310, 320, 330 comprises a polymer film with copper wire coils 350, 355, 360 secured to the film using acetone. The three tails 310, 320, 330 extend from the mail body essentially equidistantly from each other. By one approach, the coils may include a first coil 350 of wire having a first number of turns and a first surface area such that the first coil 350 has a first resonant frequency and a second coil 355 of wire having a second number of turns and a second surface area such that the second coil 355 has a second resonant frequency. In another approach, the wire may be printed on to the tail body. In the example of FIG. 3, each coil 350, 355, 360 includes 4 rows of 25 turns of wire for a total of 100 turns. The wire is a copper wire of American Wire Gauge 48 (0.0012 inch or 0.0315 millimeter diameter). The coils 350, 355, 360 have lengths of 2.0 millimeters, 3.7 millimeters, and 4.3 millimeters, respectively. According to the calculations above, the natural resonant frequencies for the coils 350, 355, 360 are 294 Hertz ("HZ"), 4.036 kHz, and 12.836 kHz. The third order frequency, 12.836 kHz, is applied to the capsule 340 by an MM device to drive the coils 350, 355, 360.

The driving circuitry 370 of the capsule 340 is configured to provide current of 10 milliamps to the coils 350, 355, 360. The driving circuitry 370 in this example is powered by a separate coil 380 that picks up the energy from the RF magnetic field of the MRI device to power the capsule 340. The coils 350, 355, 360 interact with a static magnetic field of 1 Tesla and an oscillating magnetic field applied by the MRI device to create a propulsion force of 0.04 milli-Newton. Using the MRI's magnetic field to wirelessly send energy and generate propulsion force, the capsule 340 will steer itself under the direction of the magnetic field and reach a suspected lesion and perform detailed diagnostic examination. When the capsule 340 is confined to a narrow cavity and the tail(s) contacts the surface of the cavity, an additional stick-slip mechanism comes into action, and the propulsion parallel to the cavity wall can increase significantly.

When the MM device is used to control the capsule, additional functionality can be provided to the system. In addition to providing the magnetic field that engages the coils to affect movement of the capsule, one can capture an image of the cavity including the capsule. Then, the system can mark a portion of the image with a location of the steerable capsule relative to the cavity. The image of the cavity can be created using the MRI device.

So configured, use of MRI can control the movement of such capsules in a cavity and localize the swimming-robot in cross-sectional images. This helps maneuver the capsule toward the target organ in a shorter time and reduce the overall examination time. The ability to use the MRI to maneuver the capsule arises because no ferro-magnetic material need be incorporated into the capsule. In contrast to prior legged capsules, the described design is relatively simple and easy to fabricate, and the tails do not require large motion to cause movement. The propulsive force is instead generated by multiple high frequency (12 kHz) sinusoidal signals having phase differences that create the traveling wave in the swimming tails. In addition, the high vibration frequency may prevent adhesion to the cavity walls, such as in an intestine.

Figure 5:
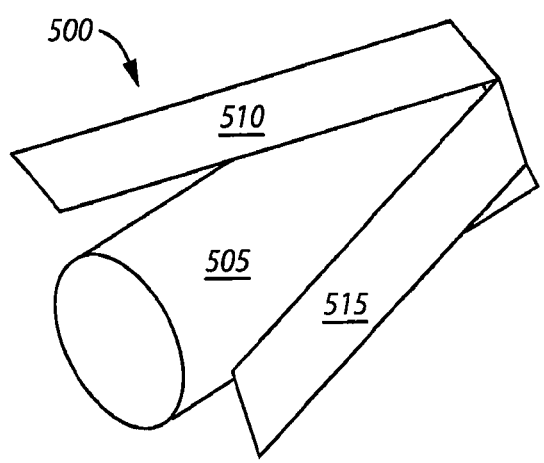
FIG. 5 comprises a perspective view of an example capsule with tails proximate to the capsule main body as configured in accordance with various embodiments of the invention.

Those skilled in the art will recognize that a wide variety of modifications, alterations, and combinations can be made with respect to the above described embodiments without departing from the spirit and scope of the invention. For example, alternative approaches can utilize alternative magnetic field sources. In another example modification, as illustrated in FIG. 5, one or more of the tails 510 and 515 of the capsule 500 can be disposed proximate to the main body 505 wherein the tail(s) 510 and 515 extends along the main body 505 of the capsule 500 instead of extending from a distal end of the capsule 500. Such modifications, alterations, and combinations are to be viewed as being within the ambit of the inventive concept.

We claim:

1. A swimming capsule for navigation in a cavity comprising:
   a main body;
   at least one tail connected to the main body;
   at least two coils disposed on each tail such that the at least two coils are responsive to a magnetic field interacting with the at least two coils such that a force is exerted on the at least one tail;
   a driving circuit communicating with the at least two coils to provide current to the at least two coils to affect interaction with the magnetic field and control the forces exerted on the at least one tail.

2. The capsule of claim 1 wherein the main body comprises at least one of a group comprising:
   a small camera;
   a biopsy tool;
   a small container in combination with a micro pump and a micro valve;
   a communication device;
   an electrode; and
   at least one operating tool.

3. The capsule of claim 1 wherein the at least one tail comprises three tails connected to the main body.

4. The capsule of claim 3 wherein the three tails extend from the main body essentially equidistantly from each other.

5. The capsule of claim 1 wherein the at least one tail comprises at least in part a polymer film.

6. The capsule of claim 1 wherein the at least one tail extends distally from the main body.

7. The capsule of claim 1 wherein the at least one tail is disposed proximate to the main body.

8. The capsule of claim 1 wherein the at least two coils comprise
- a first coil of wire having a first number of turns and a first surface area such that the first coil has a first resonant frequency;
- a second coil of wire having a second number of turns and a second surface area such that the second coil has a second resonant frequency.

9. The capsule of claim 1 wherein a magnetic resonance imaging device provides the magnetic field.

10. The capsule of claim 1 wherein the magnetic field comprises a constant magnetic field that aligns the capsule with respect to the constant magnetic field.

11. The capsule of claim 1 wherein the magnetic field comprises a varying magnetic field that induces a varying current in the at least two coils, and at least one of the at least two coils is connected to the main body such that the current provides power to at least a portion of the main body.

12. The capsule of claim 11 wherein the driving circuitry is powered by the current such that the driving circuitry controls the at least one tail.

13. The capsule of claim 1 wherein the magnetic field comprises a sinusoidal-varying magnetic field that induces a variable current in the at least two coils that induces varying deformation substantially in accordance with a sinusoidal waveform in the at least one tail.

14. The capsule of claim 1 wherein the driving circuitry is configured to provide a varying current to the at least two coils such that the interaction with the magnetic field affects varying forces on the at least one tail and varying deformation in the at least one tail.

15. The capsule of claim 1 wherein the force exerted on the at least one tail flexes the at least one tail.

16. A method comprising:
- providing a steerable capsule comprising:
- a main body;
- at least one tail coupled to the main body;
- at least two coils disposed on each tail;
- disposing the steerable capsule in a cavity;
- providing a magnetic field that engages the at least two coils to affect movement of the steerable capsule.

17. The method of claim 16 wherein providing the magnetic field that engages the at least two coils to affect movement of the steerable capsule further comprises providing a constant magnetic field that aligns the steerable capsule with respect to the constant magnetic field.

18. The method of claim 16 wherein providing the magnetic field that engages the at least two coils to affect movement of the steerable capsule further comprises providing a varying magnetic field that induces a current in the at least two coils.

19. The method of claim 18 wherein at least one of the coils is connected to the main body such that the current provides power to at least a portion of the main body.

20. The method of claim 16 wherein providing the magnetic field that engages the at least two coils to affect movement of the steerable capsule further comprises providing a sinusoidal-varying magnetic field that induces a variable current in the at least two coils that induces varying deformation substantially in accordance with a sinusoidal waveform in the at least one tail.

21. The method of claim 16 further comprising:
- capturing an image of the cavity;
- marking a portion of the image with a location of the steerable capsule relative to the cavity.

22. The method of claim 21 wherein capturing an image of the cavity further comprises taking an image of the cavity using a magnetic resonance imaging device.

23. A method of controlling movement of a capsule in a fluid or small space environment comprising:
- providing a current to at least two coils disposed on at least one tail coupled to a main body of the capsule;
- controlling the current so as to control interaction between the at least two coils and a magnetic field applied to the coils.

24. The method of claim 23 wherein the step of controlling the current further comprises varying the current to affect varying forces on the at least two coils to affect bending of each tail having coils receiving the current.

25. The method of claim 23 wherein the step of controlling the current further comprises providing a substantially constant current to the at least two coils to affect interaction between coils receiving the current and the magnetic field applied to the coils.

* * * * *

UNITED STATES PATENT AND TRADEMARK OFFICE
CERTIFICATE OF CORRECTION

PATENT NO. : 8,496,573 B2
APPLICATION NO. : 12/600163
DATED : July 30, 2013
INVENTOR(S) : Nobuhiko Hata et al.

Page 1 of 1

It is certified that error appears in the above-identified patent and that said Letters Patent is hereby corrected as shown below:

Title Page 2, (Other Publications) under item (56), Column 1, Line 11; delete "Robitics" and insert -- Robotics --, therefor;

Title Page 2, (Other Publications) under item (56), Column 1, Line 18; delete "Mediciine" and insert -- Medicine, --, therefor;

Title Page 2, (Other Publications) under item (56), Column 1, Line 50; delete "DOF" and insert -- DOF." --, therefor.

IN THE SPECIFICATION:

Column 1, Lines 6-8; delete "This application claims the benefit of U.S. Provisional application No. 60/938,909, filed May 18, 2007, which is incorporated by reference in its entirety herein." and insert -- This application is a U.S. national phase application filed under 35 U.S.C. § 371 of international application PCT/US2008/063972, filed on May 16, 2008, designating the United States, which claims the benefit of U.S. Provisional application No. 60/938,909, filed May 18, 2007, each of which is incorporated by reference in their entirety herein. --, therefor.

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,496,573 B2  
APPLICATION NO. : 12/600163  
DATED : July 30, 2013  
INVENTOR(S) : Hata et al.

Page 1 of 1

It is certified that error appears in the above-identified patent and that said Letters Patent is hereby corrected as shown below:

IN THE SPECIFICATION:

Column 1, line 14, please insert for the first paragraph of the text of the patent:

-- "This invention was made with Government support under Grant No.(s) DAMD17-02-2-0006 and W81XWH-07-2-0011 awarded by the U.S. Department of the Army and RR019703 awarded by the National Institute of Health. The Government has certain rights in this invention." --

Signed and Sealed this  
Seventeenth Day of June, 2014

Michelle K. Lee  
*Deputy Director of the United States Patent and Trademark Office*